US006838583B2

(12) United States Patent
Harper et al.

(10) Patent No.: US 6,838,583 B2
(45) Date of Patent: Jan. 4, 2005

(54) NON-HALOGENATED NAPHTHOL COMPOUNDS, ANTIMICROBIAL COMPOSITIONS CONTAINING THE SAME, AND THE METHODS OF USING THE SAME

(75) Inventors: David Scott Harper, Glen Rock, NJ (US); Robert A. Coburn, Williamsville, NY (US); Andre Soshinsky, Randolph, NJ (US); Constantine Georgiades, East Brunswick, NJ (US); Marianne D. Huntley, Morristown, NJ (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 0 days.

(21) Appl. No.: 10/441,590

(22) Filed: May 20, 2003

(65) Prior Publication Data

US 2004/0010046 A1 Jan. 15, 2004

Related U.S. Application Data

(63) Continuation of application No. 10/026,572, filed on Dec. 20, 2001, now abandoned.
(60) Provisional application No. 60/256,787, filed on Dec. 20, 2000.

(51) Int. Cl.[7] ............................................. C07C 39/12
(52) U.S. Cl. ..................... 568/719; 424/49; 514/682; 514/729; 514/732; 568/337; 568/735; 568/736
(58) Field of Search ................... 568/719, 735, 568/736, 337; 514/682, 729, 732; 424/49

(56) References Cited

U.S. PATENT DOCUMENTS

| 4,833,164 | A | * | 5/1989 | Batt ........................... 514/347 |
| 5,188,821 | A | * | 2/1993 | Gaffar et al. .................. 424/52 |
| 5,192,531 | A | * | 3/1993 | Gaffar et al. .................. 424/52 |
| 6,121,315 | A | * | 9/2000 | Nair et al. ................... 514/494 |

FOREIGN PATENT DOCUMENTS

| EP | 851300 | * | 7/1998 |
| FR | 2165741 | | 12/1971 |
| GB | 1 355 109 | | 6/1974 |
| JP | 63-88117 | * | 4/1988 |
| WO | 92/10992 | | 7/1992 |
| WO | 97/10800 | | 3/1997 |
| WO | 02/02098 A2 | | 1/2002 |

OTHER PUBLICATIONS

Khorana, J. Pharm. Sci., vol. 56, pp. 993–997 (1967).*
Carnduff, Chem. Comm., vol. 16, pp. 829–830 (1967).*
Kruber, Chem. Ber., vol. 84, pp. 831–833 (1951).*
M.I. Aguilar, et al., "Bioactive Compounds from lostephane Heterophylla (asteranceae)", Natural Product Letters, vol. 15, No. 2, 2001, pp. 93–101, no translation.

* cited by examiner

Primary Examiner—Michael L. Shippen
(74) Attorney, Agent, or Firm—Darryl C. Little; Evan J. Federman

(57) ABSTRACT

An antimicrobial compound, composition containing such compound, and method of use of the same for reducing the presence of microorganism on a substrate or in a fluid environment comprising an antimicrobial effective carrier and one or more essential antimicrobial compounds including non-halogenated naphthol compounds.

1 Claim, No Drawings

NON-HALOGENATED NAPHTHOL COMPOUNDS, ANTIMICROBIAL COMPOSITIONS CONTAINING THE SAME, AND THE METHODS OF USING THE SAME

This application is a continuation of Ser. No. 10/026,572 filed Dec. 20, 2001 now abandoned which claims the benefit of U.S. Provisional Patent Application No. 60/256,787, filed on Dec. 20, 2000, the entirety of which is hereby incorporated by reference as if fully set forth herein.

FIELD OF THE INVENTION

The present invention relates to antimicrobial compounds, and compositions containing such compounds, and more particularly to non-halogenated naphthol compounds exhibiting antimicrobial activity, antimicrobial compositions containing non-halogenated naphthol compounds, and methods of using such compositions.

BACKGROUND OF THE INVENTION

Recently, attention has focused on personal hygiene in light of mounting concerns about public health. There is a growing awareness of various microorganisms and microbial pathogens such as yeast, fungi, bacteria, molds and viruses, that can cause disease upon access and entry into the body such as through the eyes, ears, nose, mouth and skin. These microbes are generally transmitted from a source (e.g. a contaminated surface) by the hands to a person's body. Thus, a number of illnesses may easily be prevented by decontamination of the skin and the hands. In a related vein, the control of pathogenic or otherwise undesirable microbes is also a concern in promoting good oral hygiene, where reducing populations of microorganisms on the teeth, gums and tongue has been shown useful in controlling dental plaque accumulation, gingivitis, oral malodor, and other oral maladies.

It has been shown that at least 18 percent of the population is afflicted with some form of a microbial infection of the dermis. Although such infections are more common in third world areas, there is also a substantial incidence of the infections in developed areas where a high level of personal hygiene exists. Studies have further shown that the factors that contribute to rising incidence of such infections include longer lifespans, emerging resistance of microbes to antibiotics, increased use of antineoplastic agents, and a growing population of patients with some deterioration in their immune system.

Microbial infections and disease are caused by many types of microorganisms. Most infections are typically the result of microbial infection and/or the presence of microorganisms such as on the skin of the hand or foot, for example. Accordingly, it has been noted that effective treatments of such infections should also include proper preventive measures, specifically, thorough sanitization of the skin including the hands and contact surfaces to prevent further contamination and/or transmission to other individuals.

Treatment of infection typically includes the application of topical or systemic antibiotic/antifungal agents. Such therapies are disadvantageous because they exhibit a limited rate of success, are contraindicated and/or have undesirable drug interactions, produce elevated levels of toxicity, and/or are expensive. Additionally, the scientific and medical communities have moved away from the use of such systemic antimicrobial therapy for oral and general infection control due to an increase in the number of resistant strains of pathogenic microbes.

Antimicrobial cleansing compositions for use on the hands, skin, and scalp have used a variety of antimicrobial ingredients including anionic surface-active agent (e.g. sodium lauryl sulfate), coal tar, cationic antimicrobial agents such as chlorhexidine, and halogenated nonionic antimicrobial agents such as triclosan and hexachlorophene.

In addition to being present external to the body, microorganisms are also present in the oral cavity. Among undesirable microorganisms are Gram-positive and Gram-negative bacterial species associated with the formation of dental plaque (a dense, enamel-adherent biofilm consisting of microorganisms and their attendant extracellular matrix). Dental plaque is initially soft and removable by mechanical oral hygiene, but can undergo mineralization to form hard deposits of dental calculus. Although dental plaque may form on any part of the tooth surface, accumulation of plaque at the gingival margin is particularly implicated in the occurrence of gingivitis. Even with good oral hygiene, it has been shown that microorganisms (include those responsible for plaque formation) rapidly multiply and build up in the oral cavity, and many individuals have difficulty in maintaining good plaque control with brushing and flossing alone.

Specific areas, including periodontal and subgingival spaces, as well as interpapillary spaces of the tongue and tonsils provide a favorable environment for harboring bacteria and other microbes. Quite often the use of dentifrices such as toothpaste, and/or toothbrushes, dental flosses, and cosmetic mouthrinses, is insufficient to control the undesirable microorganisms. The persistence of these microorganisms in such environments greatly increases the risk of plaque and calculus buildup, which in turn presents a danger of gingival inflammation and more advanced forms of periodontal disease. In addition, the production of malodorous volatile compounds by accumulated populations of anaerobic microorganisms in dental plaque or on the tongue dorsum may lead to perceptible oral malodor.

Accordingly, it is highly desirable to include antimicrobial (antibacterial) agents in topical or oral compositions having biocidal and/or biostatic activity against a variety of microorganisms. Microorganisms of concern in hand and skin care include Gram-negative bacteria such as *Escherichia coli* and *Pseudomonas aeruginosa*, Gram positive bacteria such as *Staphylococcus aureus* and *Propionibacterium acnes*, molds such as *Aspergillus niger* and *Penicillium funiculosum*, yeasts such as *Candida albicans, Saccharomyces cerevisiae* and *Pityrosporum ovale*, dermatophytic fungi such as *Trichophyton rubrum*, microalgae such as *Chlorella* spp. and *Spyrogyra* spp., and viruses such as Herpes virus and Picornavirus. Microorganisms of concern in dental plaque, gingivitis, malodor and other oral maladies in the oral cavity include *Fusobacterium nucleatum, Prevotella intermedia, Actinomyces viscosus, Streptococcus sanguis, Streptococcus mutans*, and *Candida albicans*.

One type of oral composition used as a standard in oral hygiene is mouthrinse. However, many mouthrinses have only been effective in masking halitosis. These include mouthrinses which comprise quaternary amines (e.g., combinations of ethanol and domiphen bromide and/or cetylpyridinium chloride) or mixtures of orally acceptable surface-active agents or surfactants. Several mouthrinses that have been marketed for the reduction of plaque and gingivitis generally rely on cationic agents such as chlorhexidine digluconate, metallic fluoride salts such as stannous fluoride, antimicrobial essential oils (e.g., thymol, eucalyptol, ethanol, menthol and methyl salicylate), and/or water-insoluble phenolic agents such as triclosan.

The cationic antimicrobial materials such as chlorhexidine, benzethonium chloride, and cetyl pyridinium chloride have been investigated as antimicrobial agents for the control of gingivitis and/or oral malodor. The antimicrobial activity of these materials is theorized to be linked to the cationic charge(s) of the molecule. This charge is attracted to negatively-charged moieties on the cell membrane or wall of the microorganism, and facilitates attachment to the surface of the microorganism. The attachment and subsequent interaction with the cell surface disrupts the cell membrane structure, causing leakage of the intracellular fluids, eventually killing the microorganism. However, such materials are generally not effective when formulated in combination with anionic materials and when other cationic minerals and organic molecules present in hard water which may interfere with attraction and subsequent attachment of the cationic materials to the negatively-charged moieties. These chemical interactions may thereby reduce the overall antimicrobial efficacy of this class of compounds. Noncationic antimicrobial materials, on the other hand can be compatible with anionic components of an oral antimicrobial composition or other type of compositions containing an antimicrobial agent.

Halogenated hydroxydiphenyl ethers such as triclosan have been effectively employed in oral compositions as antimicrobial agents. However, halogenated compounds may present safety issues.

Alternatives to triclosan with similar antimicrobial activity have been the subject of continuing investigation. Alkyl substituted phenols, such as thymol (2-isopropyl-5-methyl phenol), are well known and widely used as antimicrobials. In combination with menthol, eucalyptol, and methyl salicylate, thymol is an active antimicrobial agent, for example, in commercial clinically effective anti-plaque/anti-gingivitis mouthrinse formulations. However, such essential oil formulations possess lower antimicrobial potency than those containing triclosan. Non-halogenated alternatives to triclosan with similar or improved antimicrobial activity have been the subject of inventors' investigation.

Accordingly, it would be a significant advance in the art of personal and dental hygiene to provide new non-halogenated nonionic antimicrobial compounds and compositions containing such compounds which exhibit substantial antimicrobial effectiveness and yet do not possess the safety concerns often associated with halogenated compounds such as triclosan.

SUMMARY OF THE INVENTION

2. In accordance with the present invention, non-halogenated naphthol compounds exhibiting effective antimicrobial activity are disclosed. In one aspect of the invention, the non-halogenated naphthol compounds are disclosed having the Formula

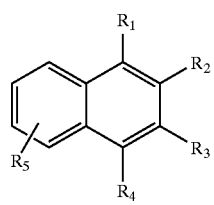

(Ia)

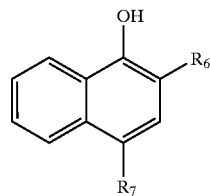

(Ib)

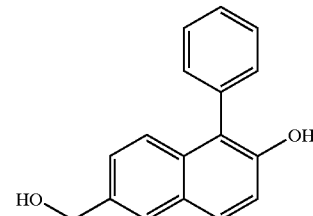

(Ic)

wherein
one of $R_1$ and $R_2$ is hydroxyl, and the other of $R_1$ and $R_2$ is selected from the group consisting of hydrogen, an alkyl group optionally substituted with hydroxyl, a cycloalkyl group optionally substituted with hydroxyl, and an hydroxyphenyl group;
$R_3$ is selected from the group consisting of hydrogen and an alkyl group optionally substituted with hydroxyl;
$R_4$ is selected from the group consisting of hydrogen, a $C_2$ to $C_6$ straight chain or branched alkyl group optionally substituted with hydroxyl, a hydroxycycloalkyl group, and

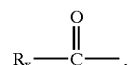

wherein $R_x$ is an alkyl group;
$R_5$ is selected from hydrogen, an alkyl group optionally substituted with hydroxyl, a cycloalkyl group, a cycloalkenyl group, an alkyl group substituted with phenyl, benzyl substituted with an alkyl group, and

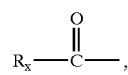

wherein $R_x$ is an alkyl group;
each of $R_6$ and $R_7$ are selected from the group consisting of straight chain or branched alkyl optionally substituted with hydroxyl, and benzy or phenyl optionally substituted with hydroxyl, alkyl, or alkoxy groups;
with the proviso that:
when $R_1$ is hydroxyl, then $R_2$, $R_3$, $R_4$, and $R_5$ are not all hydrogen;
when $R_2$ is hydroxyl, then $R_1$, $R_3$, $R_4$, and $R_5$ are not all hydrogen;
when $R_2$ is hydroxyl, then $R_5$ is not methyl;
when $R_2$ is hydroxyl and each of $R_3$, $R_4$, and $R_5$ is hydrogen, then $R_1$ is not selected from the group consisting of isopropyl and isobutyl;
when $R_1$ is hydroxyl and each of $R_3$, $R_4$ and $R_5$ is hydrogen, then $R_2$ is not 4-hydroxyphenyl; and
when $R_1$ is hydroxyl and each of $R_3$, and $R_5$ is hydrogen, then $R_2$ and $R_4$ are not both tert-butyl; and
with the further proviso that $R_6$ and $R_7$ are not both tert-butyl.

In another aspect of the present invention, an antimicrobial composition comprising an effective amount of one or more antimicrobial agents includes non-halogenated naphthol compounds for reducing the presence of microorganisms on a substrate or in a fluid environment in combination with an effective carrier. In a further aspect of the invention there is provided an oral antimicrobial composition comprising an orally acceptable carrier, and an effective antimicrobial amount of one or more antimicrobial agents including non-halogenated naphthol compounds for reducing the presence of microorganisms in an oral cavity.

In one aspect of the present invention there is provided an antimicrobial composition comprising an antimicrobial effective amount of at least one antimicrobial agent having the Formula:

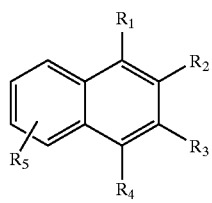
(IIa)

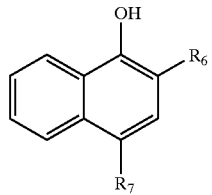
(IIb)

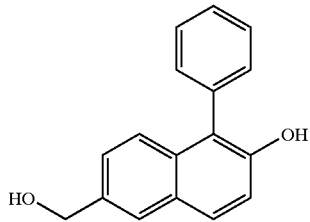
(IIc)

wherein
one of $R_1$ and $R_2$ is hydroxyl, and the other of $R_1$ and $R_2$, and each of $R_3$, $R_4$, and $R_5$ are independently selected from the group consisting of hydrogen; hydroxyl; an alkyl group optionally substituted with hydroxyl; an alkenyl group; a cycloalkenyl group; an alkyl group substituted with phenyl in which the phenyl may be substituted with a member selected from the group consisting of an alkyl group optionally substituted with hydroxyl and a cycloalkyl group optionally substituted with hydroxyl; a cycloalkyl group optionally substituted with hydroxyl; phenyl; phenyl substituted with a member selected from the group consisting of an alkyl group optionally substituted with hydroxyl, a cycloalkyl group optionally substituted with hydroxyl, and an alkoxy group; and

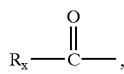

wherein $R_x$ is a member selected from the group consisting of an alkyl group, benzyl, and phenyl; and each of $R_6$ and $R_7$ are selected from the group consisting of straight chain or branched alkyl groups optionally substituted with hydroxyl, benzyl, and phenyl optionally substituted with alkyl or alkoxy groups;
with the proviso that:
when $R_1$ is hydroxyl, then $R_2$, $R_3$, $R_4$, and $R_5$ are not all hydrogen;
when $R_2$ is hydroxyl, then $R_1$, $R_3$, $R_4$, and $R_5$ are not all hydrogen;
when $R_1$ is hydroxyl, and each of $R_3$ and $R_5$ is hydrogen, then $R_2$ and $R_4$ are not independently selected from methyl and hydrogen;
when $R_2$ is hydroxyl, and each of $R_1$, $R_3$, $R_4$ is hydrogen, then $R_5$ is not methyl;
when $R_1$ is hydroxyl, and each of $R_3$, $R_4$ and $R_5$ is hydrogen, then $R_2$ is not isobutyl; and
when $R_2$ is hydroxyl and each of $R_3$, $R_4$, and $R_5$ is hydrogen, then $R_1$ is not selected from the group consisting of isopropyl and isobutyl;
with the further proviso that $R_6$ and $R_7$ are not both tert-butyl; and
an antimicrobial effective carrier.

In another aspect, the present invention is directed to an oral composition comprising an antimicrobial effective amount of at least one antimicrobial agent having the Formula

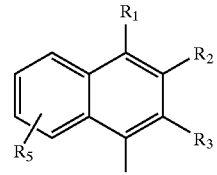
(IIIa)

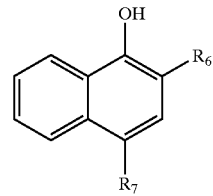
(IIIb)

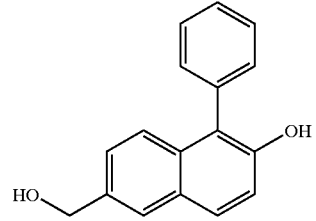
(IIIc)

wherein
one of $R_1$ and $R_2$ is hydroxyl, and the other of $R_1$ and $R_2$, and each of $R_3$, $R_4$, and $R_5$ are independently selected from the group consisting of hydrogen; hydroxyl; an alkyl group optionally substituted with hydroxyl; an alkenyl group; a cycloalkenyl group; an alkyl group substituted with phenyl in which the phenyl may be substituted with a member selected from the group consisting of an alkyl group optionally substituted with hydroxyl and a cycloalkyl group optionally substituted with hydroxyl; a cycloalkyl group optionally substituted with hydroxyl; phenyl; phenyl substituted with a member selected from the group consisting of an alkyl group optionally substituted with hydroxyl, a cycloalkyl group optionally substituted with hydroxyl, and an alkoxy group; and

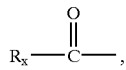

wherein $R_x$ is a member selected from the group consisting of an alkyl group, benzyl, and phenyl;

and each of $R_6$ and $R_7$ are selected from the group consisting of straight chain or branched alkyl optionally substituted with hydroxyl, and benzyl or phenyl optionally substituted with hydroxyl, alkyl, or alkoxy groups; with the proviso that:

when $R_1$ is hydroxyl, then $R_2$, $R_3$, $R_4$, and $R_5$ are not all hydrogen;

when $R_2$ is hydroxyl, then $R_1$, $R_3$, $R_4$, and $R_5$ are not all hydrogen;

and an orally acceptable carrier.

DETAILED DESCRIPTION OF THE INVENTION

The present invention is directed to non-halogenated naphthol compounds which exhibit effective antimicrobial activities in a variety of compositions and applications while maintaining a positive safety profile desirable for human use. The antimicrobial activity of the compounds of the present invention are much improved over those exhibited by prior art antimicrobial compounds. Since the novel compounds are composed entirely of hydrocarbon constituents with a hydroxyl substitutent, such compounds are significantly safer than prior art antimicrobial compounds such as halogenated naphthols, for example. More specifically, the novel compounds include one or more substitutents which substantially improves overall antimicrobial activity for effectively reducing the presence of microorganisms.

The present invention is further directed to an antimicrobial composition effective in treating various substrate surfaces including the oral cavity which may contain microorganisms. The antimicrobial composition is especially effective against microorganisms residing in the oral cavity responsible for bad breath, plaque and/or calculus, and the resulting tooth and gum diseases that may be caused thereby. The antimicrobial composition is effective yet is safe to use.

Accordingly, the present invention provides for non-halogenated naphthol compounds exhibiting antimicrobial activities which are represented by Formula:

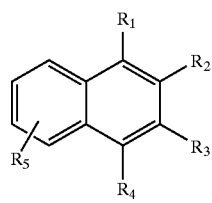
(Ia)

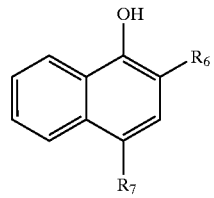
(Ib)

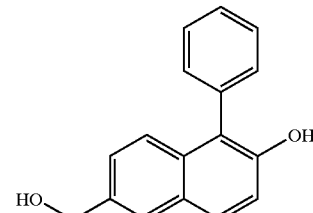
(Ic)

wherein
one of $R_1$ and $R_2$ is hydroxyl, and the other of $R_1$ and $R_2$ is selected from the group consisting of hydrogen, an alkyl group optionally substituted with hydroxyl, a cycloalkyl group optionally substituted with hydroxyl, and an hydroxyphenyl group;

$R_3$ is selected from the group consisting of hydrogen and an alkyl group optionally substituted with hydroxyl;

$R_4$ is selected from the group consisting of hydrogen, a $C_2$ to $C_6$ straight chain or branched alkyl group optionally substituted with hydroxyl, a hydroxycycloalkyl group, and

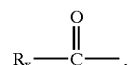

wherein $R_x$ is an alkyl group;

$R_5$ is selected from hydrogen, an alkyl group optionally substituted with hydroxyl, a cycloalkyl group, a cycloalkenyl group, an alkyl group substituted with phenyl, benzyl substituted with an alkyl group, and

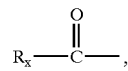

wherein $R_x$ is an alkyl group;

each of $R_6$ and $R_7$ are selected from the group consisting of straight chain or branched alkyl optionally substituted with hydroxyl, and benzyl or phenyl optionally substituted with hydroxyl, alkyl, or alkoxy groups;

with the proviso that:
when $R_1$ is hydroxyl, then $R_2$, $R_3$, $R_4$, and $R_5$ are not all hydrogen;

when $R_2$ is hydroxyl, then $R_1$, $R_3$, $R_4$, and $R_5$ are not all hydrogen;

when $R_2$ is hydroxyl, then $R_5$ is not methyl;

when $R_2$ is hydroxyl and each of $R_3$, $R_4$, and $R_5$ is hydrogen, then $R_1$ is not selected from the group consisting of isopropyl and isobutyl;

when $R_1$ is hydroxyl and each of $R_3$, $R_4$ and $R_5$ is hydrogen, then $R_2$ is not 4-hydroxyphenyl; and when $R_1$ is hydroxyl and each of $R_3$, and $R_5$ is hydrogen, then $R_2$ and $R_4$ are not both tert-butyl;

with the further proviso that $R_6$ and $R_7$ are not both tert-butyl.

A particularly preferred group of compounds exhibiting antimicrobial properties includes 3-isopropyl-6-(1-methyl-butyl)-naphthalen-2-ol, 3-isopropyl-6-(1-phenyl-ethyl)-naphthalen-2-ol, 1-(4-hydroxynaphthyl)octan-1-one, 6-(1-ethyl-1-methyl-propyl)-1-isopropyl-naphthalen-2-ol, 6-(tert-butyl)-1-isoproyl-naphthalen-2-ol, 6-(3-cyclohexenyl)-2-naphthol, 1-(6-hydroxy-2-naphthyl)hexan-1-one, 1-isopropyl-6-(3-methyl-benzyl)-naphthalen-2-ol, 1-(4-hydroxynaphthyl)hexan-1-one, 6-cyclohex-2-enyl-3-isopropyl-naphthalen-2-ol, 6-cyclopentyl-2-naphthol, 6-(1-ethyl-1-methyl-propyl)-3-isopropyl-naphthalen-2-ol, 3-isopropyl-6-(3-methyl-benzyl)naphthalen-2-ol, 6-(tert-butyl)-1-isopropyl-naphthalen-2-ol, 6-(3-methyl-benzyl)-2-naphthol, 4-(2-hydroxycyclohexyl)-1-naphthol, 4-(3-hydroxycyclohexyl)-1-naphthol, 1-(2-hydroxycyclohexyl)-2-naphthol, 1-(3-hydroxycyclohexyl)-2-naphthol, 1-(4-hydroxycyclohexyl)-2-naphthol, 1-cyclopentyl-2-naphthol, 1-(2-hydroxycyclopentyl)-2-naphthol, 1-(3-hydroxycyclopentyl)-2-naphthol, 4-(2-hydroxycyclopentyl)-1-naphthol, and 4-(3-hydroxycyclopentyl)-1-naphthol.

The present invention further provides for preferred compositions comprising an antimicrobial effective amount of one or more antimicrobial agents having Formula:

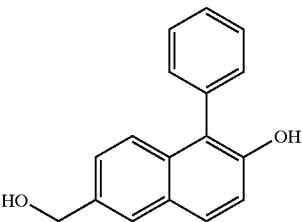

wherein
one of $R_1$ and $R_2$ is hydroxyl, and the other of $R_1$ and $R_2$, and each of $R_3$, $R_4$, and $R_5$ are independently selected from the group consisting of hydrogen; hydroxyl; an alkyl group optionally substituted with hydroxyl; an alkenyl group; a cycloalkenyl group; an alkyl group substituted with phenyl in which the phenyl may be substituted with a member selected from the group consisting of an alkyl group optionally substituted with hydroxyl and a cycloalkyl group optionally substituted with hydroxyl; a cycloalkyl group optionally substituted with hydroxyl; phenyl; phenyl substituted with a member selected from the group consisting of an alkyl group optionally substituted with hydroxyl, a cycloalkyl group optionally substituted with hydroxyl, and an alkoxy group; and

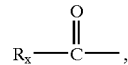

wherein $R_x$ is a member selected from the group consisting of an alkyl group, benzyl, and phenyl;
and each of $R_6$ and $R_7$ are selected from the group consisting of straight chain or branched alkyl optionally substituted with hydroxyl, and benzyl or phenyl optionally substituted with hydroxyl, alkyl, or alkoxy groups; with the proviso that:
when $R_1$ is hydroxyl, then $R_2$, $R_3$, $R_4$, and $R_5$ are not all hydrogen;
when $R_2$ is hydroxyl, then $R_1$, $R_3$, $R_4$, and $R_5$ are not all hydrogen;
when $R_1$ is hydroxyl, and each of $R_3$ and $R_5$ is hydrogen, then $R_2$ and $R_4$ are not independently selected from methyl and hydrogen;
when $R_2$ is hydroxyl, and each of $R_1$, $R_3$, $R_4$ is hydrogen, then $R_5$ is not methyl;
when $R_1$ is hydroxyl, and each of $R_3$, $R_4$ and $R_5$ is hydrogen, then $R_2$ is not isobutyl; and
when $R_2$ is hydroxyl and each of $R_3$, $R_4$, and $R_5$ is hydrogen, then $R_1$ is not selected from the group consisting of isopropyl and isobutyl;
with the further proviso that $R_6$ and $R_7$ are not both tert-butyl; and
an antimicrobial effective carrier.

The above antimicrobial agents of Formula (II), are incorporated in an antimicrobial composition of the present invention in an amount of about 0.0001 to 10% by weight, preferably from about 0.001 to 5% by weight.

A particularly preferred group of antimicrobial agents includes 1-(2-hydroxyphenyl)naphthalen-2-ol, 6-(tert-butyl)-1-isopropyl-naphthalen-2-ol, 6-(3-cyclohexenyl)-2-naphthol, 6-cyclopentyl-2-naphthol, 6-(3-methylbenzyl)-2-naphthol, 1-Isopropyl-6-(3-methyl-benzyl)-napthtalen-2-ol, 3-Isopropyl-6-(1-phenyl-ethyl)-naphthalen-2-ol, 6-(1-Ethyl-1-methyl-propyl)-3-isopropyl-naphthalen-2-ol, 6-Cyclohex-2-enyl-3-isopropyl-naphthalen-2-ol, 3-Isopropyl-6-(3-methyl-benzyl)-naphthalen-2-ol, 3-Isopropyl-6-(1-methyl-butyl)-naphthalen-2-ol, 1-(4-Hydroxy-cyclohexyl)-naphthalen-2-ol, 1-Cyclopentyl-naphthalen-2-ol, 3-(1-Ethyl-1-hydroxy-propyl)-naphthalen-2-ol, 1-(6-hydroxyhexyl)naphthalen-2-ol, 6-Hydroxymethyl-1-phenyl-naphthalen-2-ol, 2-tert-butyl-1-naphthol, 4-tert-butyl-1-naphthol, 2,4-bis-tert-butyl-1-naphthol, 4-benzyl-1-naphthol, 3-isopropyl-2-naphthol, 1-butyl-2-naphthol, 1-tert-butyl-2-naphthol, 1-hexyl-2-naphthol, 1-cyclohexyl-2-naphthol, 1-(3-hydroxycyclohexyl)-2-naphthol, 1-phenyl-2-naphthol, and 1-benzyl-2-naphthol.

The present invention also provides a method of reducing the presence of microorganisms on a substrate comprising treating the substrate with an antimicrobial effective amount of at least one antimicrobial agent having Formula (II).

The antimicrobial compositions of the present invention may be incorporated into products having a variety of vehicles for application to the skin or tissue surfaces including creams, lotions, foundations, cleansing lotions, soaps, shampoos, ointments, syrups and suspensions. Compositions may comprise, for example, aqueous or oily solutions or dispersions, oil-in-water or water-in-oil emulsions, pastes, gels or solids. Topically or orally acceptable carriers and excipients of use in such preparations will be well known to those skilled in the art.

The anti-microbial compositions of the present invention may be included in products which are developed for the treatment of microorganism-instigated conditions such as deodorant and/or antiperspirant preparations, antibacterial skin washes, anti-acne preparations, impregnated materials (e.g. wound dressings, sutures, and dental floss), pharmaceuticals, opthalmic preparations and sterilants.

Typically, a deodorizing composition reduces or prevent body odor by reducing perspiration (e.g. often referred to as an antiperspirant composition) or the presence of microorganisms on the surface of the skin.

Antiperspirant compositions often comprise a metal salt, such as aluminum or zirconium salts which blocks the pores of the skin. Typically, such compositions, however, reduce perspiration by no more than 50%. It is well known that sweat is odorless until it has been degraded by the skin microflora. Typical deodorant compositions include ethanol and/or Triclosan (2',4,4'-trichloro,2-hydroxy-diphenyl ether) which are a well known antimicrobial agents. However, the deodorizing effect obtained with such deodorant compositions is transitory and the concentration of microorganisms may reach previous levels shortly after application.

The invention provides a deodorant composition for topical application to human skin comprising at least one antimicrobial agent having Formula (II) in an acceptable carrier in which the composition is at least reduces the presence of microorganisms and/or their malodorous metabolic processes for greater than a transitory period of time.

Such deodorant compositions in addition to containing the composition of the present invention may contain a low molecular weight aliphatic alcohol, preferably containing up to 4 carbons and especially a monohydric alcohol such as ethanol, which can act in combination with the antimicrobial agents of Formula (II) to provide an effective deodorant composition. The amount of the alcohol in the composition is typically selected within the range of from about 10 to 80% by weight, preferably from about 30 to 70% by weight.

The deodorant composition according to the present invention may also comprise other materials commonly found in deodorant or antiperspirant compositions. In practice, the present composition usually contains at least one acceptable carrier in addition to the antimicrobial agent of Formula (II) alone or in combination with an alcohol. The carrier may comprise a liquid vehicle such as an alcohol as described hereinbefore, in addition to water, a hydrophobic vehicle which may for example be a volatile or non-volatile silicone oil, a liquid hydrocarbon, a water-insoluble alcohol, an aliphatic ether, an aliphatic or aromatic ester. The carrier is typically present in an amount of from about 10 to 80% by weight based on the total weight of the composition.

Other additives may include perfumes in an amount of from about 0 to 2% by weight, antiperspirant actives such as aluminum or zirconium compounds in an amount of from about 0 to 40% by weight, preferably from about 5 to 28% by weight, skin softening agents such as silicone oils or solid silicone polymers, in an amount of from about 0 to 20% by weight, coloring agents in an amount of from about 0 to 2% by weight, humectants, such as sorbitol or glycerol, in an amount of from about 0 to 10% by weight, thickening agents such as starches or cellulose derivatives, in an amount from about 0 to 5% by weight, gellants such as dibenzoyl sorbitol, hydroxystearic acid, stearyl alcohol, or amide derivatives of tricarboxylic acids, in an amount of from about 0 to 15% by weight, suspension agents, such as clays or silicas, in an amount of up to about 5% by weight, structurants such as silicone elastomers or silicone or hydrocarbon waxes, in an amount of about 0 to 15% by weight, propellants, such as hydrocarbons having a boiling point of below 10EC, e.g. butane and propane isomers, in an amount of from about 30 to 95% by weight, and other cosmetic additives conventionally employed in such compositions. Where water and a hydrophobic material is present, the composition preferably contains an emulsifier/system such as polyethoxylate ethers or esters. The use of such substances and the proportions in which they are incorporated depend on the form of the composition which may be an aerosol, stick, roll-on, gel, lotion, cream, ointment, powder, suspension or soap.

Gels are transparent, semi-solid, colloidal systems where the water is restricted by an interlacing network of solvated particles. The gels useful in the present invention may have a wide range of viscosities, e.g., from about 4,000 to about 200,000 centipoise, however, since they are formulated for topical use, the compositions will generally have relatively high viscosities (i e., they will be self-supporting).

The formulation of aqueous gels requires the presence of water and generally requires the use of a compatible pharmaceutically-acceptable gelling agent in the compositions of the present invention. Preferred compositions contain at least about 15% water, and may additionally contain an alcohol or mixture of alcohols (e.g., $C_1$–$C_{14}$) in a water:alcohol ratio of from about 5:1 to about 100:1. The gelling agent will generally be present at about 0.25% to about 10% of the composition. Desirable gels may be formed using an acidic carboxy polymer as the gelling agent, together with a compatible neutralizing agent. Pharmaceutically-acceptable acidic carboxy polymers include, for example, Carbopol compounds (a range of carboxy polymethylenes commercially available from B.F. Goodrich Chemicals, Cleveland, Ohio) and the neutralizing compounds include, for example, diisopropyl amine, sodium hydroxide, and beta-alanine. Surface active agents or surfactants, especially nonionic surfactants, such as ethylene oxide/propylene oxide block copolymers (commercially available as Pluronics from BASF Wyandotte Corp.), and/or ethylene glycol or propylene glycol may also be included in the compositions to help in the formation of the gel and to act as dispersing agents for the active components.

Aqueous lotions of the present invention are formulated in the same way as the above-described gels, except that they have lower viscosities (i.e., below about 4,000 centipoise) and do not include the gelling agent. Lotions are liquid preparations intended for external application to the skin. Most lotions contain finely powdered substances that are insoluble in the dispersion medium and are suspended through the use of suspending or dispersing agents. Other lotions have, as the dispersed liquid phase, liquid substances that are immiscible with the vehicle and are usually dispersed by means of emulsifying agents or other suitable stabilizers. Depending upon the nature of the ingredients, lotions may be prepared in the same manner as suspensions, emulsions or solutions. The fluidity of lotions permits their rapid and uniform application over a wide surface area.

The compositions of the present invention may additionally contain, at their art-established usage levels, compatible adjunct components conventionally used in the formulation of topical compositions. These adjunct components include, but are not limited to, active materials (such as supplementary antimicrobial or anti-inflammatory ingredients) or ingredients used to enhance the formulation, itself (such as excipients, dyes, perfumes, thickening agents, skin penetration enhancers, stabilizers, preservatives, and antioxidants). The compositions of the present invention may also contain, in an amount which can range from about 1% to about 99.5% of the compositions, compatible pharmaceutical carrier materials especially adapted for topical application and formulation into an aqueous lotion or gel. Carrier materials suitable for use in the instant compositions include those well-known for use in the cosmetic and medical arts. Suitable carriers include, for example, water, liquid alcohols, liquid glycols, liquid polyalkalene glycols, liquid esters, liquid amines, liquid protein hydrolysates, liquid alkalated protein hydrolysates, liquid lanolin and lanolin derivatives, and like materials.

More preferred compositions include those represented for use in an oral cavity comprise an antimicrobial effective amount of one or more antimicrobial agents having Formula

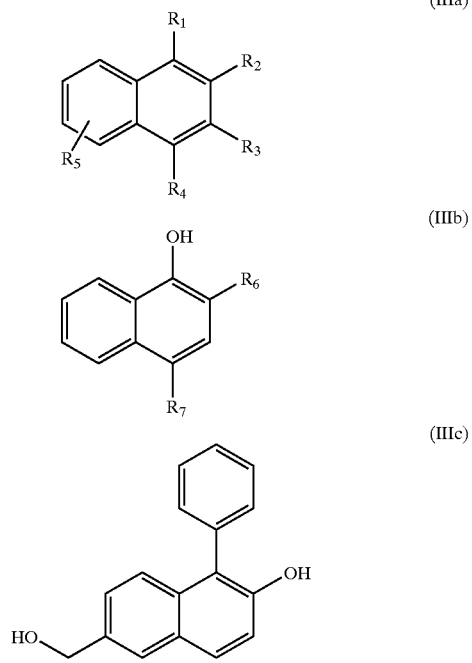

(IIIa)

(IIIb)

(IIIc)

wherein
one of $R_1$ and $R_2$ is hydroxyl, and the other of $R_1$ and $R_2$, and each of $R_3$, $R_4$, and $R_5$ are independently selected from the group consisting of hydrogen; hydroxyl; an alkyl group optionally substituted with hydroxyl; an alkenyl group; a cycloalkenyl group; an alkyl group substituted with phenyl in which the phenyl may be substituted with a member selected from the group consisting of an alkyl group optionally substituted with hydroxyl and a cycloalkyl group optionally substituted with hydroxyl; a cycloalkyl group optionally substituted with hydroxyl; phenyl; phenyl substituted with a member selected from the group consisting of an alkyl group optionally substituted with hydroxyl, a cycloalkyl group optionally substituted with hydroxyl, and an alkoxy group; and

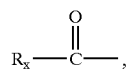

wherein $R_x$ is a member selected from the group consisting of an alkyl group, benzyl, and phenyl;
and each of $R_6$ and $R_7$ are selected from the group consisting of straight chain or branched alkyl optionally substituted with hydroxyl, and benzyl or phenyl optionally substituted with hydroxyl, alkyl, or alkoxy groups;

with the proviso that:
when $R_1$ is hydroxyl, then $R_2$, $R_3$, $R_4$, and $R_5$ are not all hydrogen;
when $R_2$ is hydroxyl, then $R_1$, $R_3$, $R_4$, and $R_5$ are not all hydrogen;
and
an orally acceptable carrier.

The present invention further provides a method of reducing microorganisms in an oral cavity which comprises administering to the oral cavity an oral antimicrobial composition having an effective amount of at least one antimicrobial agent of Formula (IIII).

A particularly preferred group of antimicrobial agents for oral composition includes 1-(2-hydroxyphenyl)naphthalen-2-ol, 6-(tert-butyl)-1-isopropyl-naphthalen-2-ol, 6-(3-cyclohexenyl)-2-naphthol, 6-cyclopentyl-2-naphthol, 6-(3-methylbenzyl)-2-naphthol, 1-Isopropyl-6-(3-methyl-benzyl)-naphthalen-2-ol, 3-Isopropyl-6-(1-phenyl-ethyl)-naphthalen-2-ol, 6-(1-Ethyl-1-methyl-propyl)-3-isopropyl-naphthalen-2-ol, 6-Cyclohex-2-enyl-3-isopropyl-naphthalen-2-ol, 3-Isopropyl-6-(3-methyl-benzyl)-naphthalen-2-ol, 3-Isopropyl-6-(1-methyl-butyl)-naphthalen-2-ol, 1-(4-Hydroxy-cyclohexyl)-naphthalen-2-ol, 1-Cyclopentyl-naphthalen-2-ol, 3-(1-Ethyl-1-hydroxy-propyl)-naphthalen-2-ol, 1-(6-hydroxyhexyl)naphthalen-2-ol, 6-Hydroxymethyl-1-phenyl-naphthalen-2-ol, 2-tert-butyl-1-naphthol, 4-tert-butyl-1-naphthol, 2,4-bis-tert-butyl-1-naphthol, and 4-benzyl-1-naphthol, 1-isopropyl-2-naphthol, 3-isopropyl-2-naphthol, 1-butyl-2-naphthol, 1-tert-butyl-2-naphthol, 1-hexyl-2-naphthol, 1-cyclohexyl-2-naphthol, 1-(3-hydroxycyclohexyl)-2-naphthol, 1-phenyl-2-naphthol, and 1-benzyl-2-naphthol.

The antimicrobial agents of Formula (III) may be present in an oral composition of the present invention in an amount of from about 0.0001 to 10% by weight, preferably from about 0.001 to about 5% by weight.

The use of the anti-microbial compositions according to the invention in oral composition is particularly advantageous because they provide effective results against a broad range of microorganisms known to be present in the oral cavity.

Oral compositions which contain antimicrobial compounds of the present invention may be in the form of mouthwashes, gargles, dentifrices, anti-plaque compositions, dispersible oral films, and as general antiseptic compositions, for example, in the form of denture cleansing tablets or solutions. The oral compositions of the present invention may, if desired, further comprise one or more additional active ingredients and formulations containing such, as conventionally used in the art. These include, for example, anti-plaque agents such as bromochlorophene, triclosan, cetylpyridinium chloride, chlorhexidine salts, and essential oils such as thymol, menthol, and the like, fluoride ion sources such as sodium fluoride, sodium monofluorophosphate and amine fluorides, anti-tartar agents such as zinc salts, preferably zinc citrate, and water soluble pyrophosphate salts, preferably alkali metal pyrophosphates, and desensitizing agents which reduce tooth sensitivity including potassium salts such as potassium nitrate and potassium chloride and strontium salts such as strontium chloride and strontium acetate.

One particular formulation comprising essential oils is sold commercially as LISTERINE® which composition is exemplified in Pan et al. (U.S. Pat. No. 6,121,315), and which reference includes effective essential oil formulations having anti-plaque activity. The contents of U.S. Pat. No. 6,121,315 is hereby incorporated by reference in its entirety.

The essential oil formulation preferably comprises from about 0.005% to 0.5% by weight of thymol, from about 0.005% to 0.5% by weight of menthol, from about 0.005% to 0.5% by weight of eucalyptol, and from about 0.005% to 0.5% by weight of methyl salicylate.

The compositions according to the invention may alternatively be provided in concentrated form, for example as a powder, anhydrous solution or effervescent tablet formulation, suitable for dilution in water prior to use as a sterilant of, for example, dental instruments. One preferred use of the anti-microbial compositions of the invention is as toothbrush sanitizers, designed to reduce microbiological contamination of toothbrush heads, for example by overnight soaking as needed, typically every 1 to 14 days of use. A substantial reduction in microorganism contamination may be achieved in this way without significant adverse effects on the toothbrush or other dental instrument.

Antimicrobial enhancing agent(s) may be included in the oral compositions of the present invention. Incorporating such antimicrobial enhancing agent into compositions containing antimicrobial compounds are known in the art, as described for example in U.S. Pat. Nos. 5,188,821 and 5,192,531. The term "antimicrobial enhancing agent" as used herein refers to organic compounds which contains a delivery-enhancing group and a retention-enhancing group which together act to improve the sanitizing effectiveness of the antimicrobial agent. As used herein, the delivery-enhancing group refers to one which attaches or substantively, adhesively, cohesively or otherwise bonds the antimicrobial enhancing agent (carrying the antimicrobial agent) to oral surfaces such as tooth and gum, thereby "delivering" the antimicrobial agent to such surfaces. The retention-enhancing group, generally hydrophobic, attaches or otherwise bonds the antimicrobial agent to the antimicrobial enhancing agent, thereby promoting retention of the antimicrobial agent to the antimicrobial enhancing agent and indirectly on the oral surfaces. The active retention of the antimicrobial agent on the oral surfaces enhances the disinfecting effect on oral surfaces.

In the preferred form, the antimicrobial enhancing agent includes an anionic polymer comprising a chain or backbone containing repeating units each preferably containing at least one carbon atom and preferably at least one directly or indirectly pendent, monovalent delivery-enhancing group, and at least one directly or indirectly pendent, monovalent retention-enhancing group geminally, vincinally, or less preferably otherwise bonded to atoms, preferably carbon, in the chain.

The antimicrobial enhancing agent may be a simple compound such as a polymerizable monomer, or more preferably a polymer including oligomers, homopolymers, copolymers of two or more monomers, ionomers, block copolymers, graft copolymers, cross-linked polymers and copolymers, and the like. The antimicrobial enhancing agent may be natural or synthetic, and water-insoluble or preferably water soluble or swellable, having an average molecular weight of from about 100 to 5,000,000, preferably from about 1,000 to 1,000,000, more preferably from about 25,000 to 500,000.

Preferable antimicrobial enhancing agents for use in the practice of the present invention include a natural or synthetic anionic polymeric polycarboxylate having a molecular weight of from about 1,000 to 5,000,000, preferably from about 30,000 to 500,000. Synthetic anionic polymeric polycarboxylates are generally employed in the form of their free acids or preferably partially or more preferably fully neutralized water soluble alkali metal such as potassium and sodium, or ammonium salts. Preferred are 1:4 to 4:1 copolymers of maleic anhydride or acid with another polymerizable ethylenically unsaturated monomer, preferably methyl vinyl ether/maleic anhydride having a molecular weight of from about 30,000 to 1,000,000, most preferably from about 30,000 to 500,000. These copolymers are available, for example, as GANTREZ®, AN 139 (molecular weight 500,000), AN 119 (molecular weight 250,000), and preferably S-97 Pharmaceutical Grade (molecular weight 700,000), from ISP Technologies, Inc., Bound Brook, N.J. 08805.

Other useful polymeric polycarboxylates containing or modified to contain retention-enhancing groups include the 1:1 copolymers of maleic anhydride with ethyl acrylate, hydroxyethyl methacrylate, N-vinyl-2-pyrollidone, or ethylene, the latter being available, for example, as Monsanto EMA® No. 1103 (molecular weight 10,000), and Grade 61, and 1:1 copolymers of acrylic acid with methyl or hydroxyethyl methacrylate, methyl or ethyl acrylate, isobutyl methacrylate, isobutyl vinyl ether or N-vinyl-2-pyrrolidone. Additional polycarboxylate compounds containing or modified to contain retention-enhancing groups include copolymers of maleic anhydride with styrene, isobutylene or ethyl vinyl ether, polyacrylic, polyitaconic and polymaleic acids, and sulfonacrylic oligomers with a molecular weight as low as 1,000 available as UNIROYAL® ND-2.

Also useful in the practice of the present invention are the so-called carboxyvinyl polymers, commercially available, for example, under the trademarks CARBOPOL® 934, 940, and 941 from B.F. Goodrich, Cleveland, Ohio 44131, these polymers consisting of a colloidally water-soluble polymer of polyacrylic acid crosslinked with from about 0.75% to about 2.0% of polyallyl sucrose or polyallyl pentaerythritol as a crosslinking agent, often with molecular weights of up to 4-5 million or more.

Polysiloxanes containing or modified to contain pendent delivery-enhancing groups and retention-enhancing groups such as liquid silicone oils such as diphenyl or $di(C_1-C_4)$ alkyl polysiloxanes and particularly dimethyl-polysiloxane, may also be employed in the practice of the present invention.

Also effective herein are ionomers containing or modified to contain delivery- and retention-enhancing groups. Ionomers are described on pages 546–573 of the Kirk Othmer Encyclopedia of Chemical Technology, Third Edition, Supplement Volume, John Wiley & Sons, copyright 1984, which description is incorporated herein by reference. Also effective herein, provided that contain or are modified to containing retention-enhancing groups, are polyesters, polyurethanes, and synthetic and natural polyamides including proteins and proteinaceous materials such as collagen, poly(arginine) and other polymerized amino acids.

The antimicrobial enhancing agent, when employed, is incorporated in the compositions of the present invention in weight amounts of from about 0.05 to about 5%, preferably from about 0.1 to 3%.

Fluoride ions may also be included in the oral compositions of the present invention. Fluoride ions are implicated in the prevention of dental caries and may also serve as a tooth-hardening agent. An amount of fluoride ions suitable for use in an oral composition of the present invention is from 25 ppm to 5,000 ppm.

Fluoride ion producing compounds vary in degree of water solubility. They release fluoride ions in water and do not generally react with other compounds of the oral composition. Among the fluoride ion producing compounds are inorganic fluoride salts, such as soluble alkali metal, alkaline earth metal salts, for example, sodium fluoride, potassium fluoride, ammonium fluoride, calcium fluoride, cuprous fluoride, zinc fluoride, barium fluoride, sodium monofluorophosphate, aluminum mono-and di-fluorophosphate and sodium calcium fluorophosphate. Alkali metal and tin fluorides, such as sodium and stannous fluorides, sodium monofluorophosphate (MFP) and mixtures thereof, are preferred.

The amount of fluoride ion producing compound is dependent upon the type of compound, its solubility in water, and the type of oral composition. A non-toxic amount of such compound is generally in the range from about 0.0005 to 3.0% by weight based on the total weight of the oral composition. Any suitable minimum amount of such compounds may be used, but it is preferable to employ a sufficient amount of the fluoride ion producing compounds to provide from about 300 to 2,000 ppm, more preferably from about 800 to about 1,500 ppm of fluoride ion to the oral cavity.

Typically, for sodium fluoride, the desired amount up to about 2% by weight, based on the total weight of the composition, and preferably in an amount of from about 0.05 to 1%, more preferably from about 0.2 to 0.35% by weight. Typically for sodium monofluorophosphate, the compound is desirably present in an amount of from about 0.1 to 3%, more preferably about 0.76% by weight.

The oral composition of the present invention may be in the form of a solution such as a mouthrinse and may be in the form of a semi-solid such as a toothpaste, a gel dentifrice (which may contain from about 0 to 75% by weight of a polishing agent), a chewing gum, a dispersible oral film, a film-forming dentifrice, a solid lozenge or the like.

Oral gel preparations typically contain a siliceous polishing material including crystalline silica having particle sizes of up to 5 microns, silica gel, colloidal silica or complex amorphous alkali metal aluminosilicate or combinations thereof. When visually clear or opacified gels are employed, a polishing agent of colloidal silica or alkali metal aluminosilicate complexes (that is, silica containing alumina combined in its matrix) are particularly useful, since they are consistent with gel-like texture and have refractive indices close to the refractive indices of gelling agent-liquid (including water and/or humectant) systems commonly used in dentifrices.

Where the oral composition of the present invention is a gel or paste, an orally acceptable carrier, including a water-phase with humectant which is preferably glycerine or sorbitol or an alkylene glycol such as polyethylene glycol or propylene glycol is present. Where water is typically present in an amount of from about 15 to 40% by weight and glycerine, sorbitol and/or the alkylene glycol (preferably propylene glycol) are preferably in an amount of from about 20 to 75% by weight, preferably about 25 to 60% by weight based on the total weight of the composition.

When the oral composition is substantially semi-solid or pasty in character, such as a toothpaste (dentifrice), the orally acceptable carrier of the dentifrice may contain a dentally acceptable polishing material such as sodium bicarbonate, sodium metaphosphate, potassium metaphosphate, tricalcium phosphate, dihydrated dicalcium phosphate, anhydrous dicalcium phosphate, calcium pyrophosphate, calcium carbonate, aluminum silicate, hydrated alumina, silica, bentonite, and mixtures thereof alone or with minor amounts of hard polishing material such as calcined alumina and/or zirconium silicate. Preferred polishing materials include sodium bicarbonate, silica, sodium metaphosphate, dicalcium phosphate, calcium pyrophosphate and hydrated alumina.

The polishing material is generally present in the oral composition in an amount of from about 10% to 75% by weight, preferably from about 10% to 30% by weight in a gel, and preferably from about 25% to 75% by weight in a cream or paste.

Toothpastes or dental cream dentifrices as well as gel dentifrices typically contain a natural or synthetic thickener or gelling agent in an amount of from about 0.1 to 10% by weight, preferably from about 0.5 to 5% by weight.

Suitable thickeners or gelling agents include Irish moss, iota-carrageenan, kappa-carrageenan, gum tragacanth, starch, polyvinylpyrrolidone, xantham gum, hydroxyethyl propyl cellulose, hydroxybutyl methyl cellulose, hydroxypropyl methyl cellulose, hydroxyethyl cellulose and sodium carboxymethyl cellulose.

Where the oral composition is a liquid such as a mouthwash or rinse, the liquid carrier is typically a water-alcohol mixture. Generally, the weight ratio of water to alcohol is in the range of from about 3:1 to 20:1 and preferably from about 4:1 to 10:1. The alcohol is a non-toxic alcohol such as ethanol or isopropanol. A humectant such as glycerine, sorbitol or an alkylene glycol such as polyethylene glycol or preferably propylene glycol may be present in an amount of from about 10 to 30% by weight. Mouthrinses typically contain about 50 to 85% of water, from about 0 to 20% by weight of a non-toxic alcohol and from about 10 to 40% by weight of a humectant.

Organic surface-active agents may be used in the compositions of the present invention to achieve increased antimicrobial action, and assist in achieving thorough and complete dispersion of the antimicrobial agent of Formula (III) throughout the oral cavity. The organic surface-active agent is preferably anionic, cationic, nonionic or ampholytic in nature, and imparts to the composition detersive and foaming properties. Suitable examples of anionic surface-active agents are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals and alkoyl taurines, and the like. Examples of such compounds include N-lauroyl sarcosine, and the sodium, potassium and ethanolamine salts of N-lauroyl, N-myristoyl, or N-palmitoyl sarcosine which are substantially free from soap or similar higher fatty acid material as well as N-methyl-N-cocoyl (or oleoyl or palmitoyl) taurines. The use of sarcosinate compounds in the oral compositions of the present invention is typically advantageous since these materials exhibit a prolonged and marked effect in the inhibition of acid formation in the oral cavity due to carbohydrate breakdown in addition to exerting some reduction in the solubility of tooth enamel in acid solutions.

Examples of water-soluble nonionic surface-active agents are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide.

Amphoteric surface active agents have the capacity to behave as either an acid or a base and include quaternized imidazole derivatives. Preferred amphoteric surfactants include long chain (alkyl) amino-alkylene alkylated amine derivatives, also known as MIRANOL®, manufactured by Rhone-Poulanc, Cranberry, N.J.

Examples of polyoxamers useful in the practice of the present invention include block copolymers of polyoxyethylene and polyoxypropylene having an average molecular weight of from about 3000 to 5000 and a preferred average molecular weight of from about 3500 to 4000, and containing from about 10 to 80% by weight of hydrophilic polyoxyethylene groups of the block copolymer.

Natural and artificial sweeteners may be used in the oral compositions. The sweetener may be selected from a wide range of well known materials including naturally occurring water-soluble sweeteners, artificial water-soluble sweeteners and modified water-soluble sweeteners derived from naturally occurring water-soluble sweeteners. Artificial water-soluble sweeteners include, but are not limited to, soluble saccharin salts, e.g., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin and dipeptide based sweeteners, such as L-aspartic acid derived sweeteners. Dipeptide sweeteners include L-aspartyl-L-phenylalanine methyl ester (Aspartame) and materials described in U.S. Pat. No. 3,492,131, L-alpha-aspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenylglycine, L-aspartyl-2,5-dihydro-L-phenylalanine and L-aspartyl-L-(1-cyclohexene)-alanine. Naturally occurring water-soluble sweeteners include, but are not limited to, sugar alcohols, including sorbitol as 70% sorbitol solution, mannitol, xylitol, maltitol, hydrogenated starch hydrolysates and mixtures thereof.

Water-soluble sweeteners derived from naturally occurring water-soluble sweeteners include, but are not limited to, chlorinated derivatives of sucrose, known, for example, under the product designation of Sucralose, and protein-based sweeteners such as thaumaoccous danielli (Thaumatin I and III).

Sorbitol solution supplies sweetness and body to the composition and gives a desirable mouth feel. Sorbitol solution also enhances flavor, prevents harsh taste and provides a fresh and lively sensation in the mouth. It also adds body and serves as a humectant.

In general, an effective amount of sweetener is utilized to provide the level of sweetness desired in any particular embodiment of the oral compositions according to the present invention. This amount will vary with the sweetener selected and the final form of the oral composition. The amount of sweetener normally present is from about 0.0025% by weight to about 60% by weight of the oral composition. The exact range of amounts for each type of sweetener in an oral composition is readily determined by those skilled in the art.

The flavors that may be used in the invention include natural and artificial flavors known in the art. Suitable flavors include, but are not limited to, mints, such as peppermint, citrus flavors such as orange and lemon, artificial vanilla, cinnamon, various fruit flavors, and the like. Anethole (or anise camphor, p-propenyl anisole) is a flavor constituent of anise and fennel oils that are used widely as flavoring agent and antiseptic and was found useful in masking the harsh taste of thymol.

The amount of flavor is normally a matter of preference subject to the type of final oral composition, the individual flavor employed and the strength of flavor desired. The flavors are preferably utilized in amounts that may range of from about 0.01% to about 6% by weight of the oral composition.

Coloring agents are used in amounts effective to produce an oral composition of the desired color. These coloring agents may be incorporated in amounts up to about 3% by weight of the oral composition. The coloring agents may also include natural food colors and dyes suitable for food, drug and cosmetic applications. These coloring agents are known as FD & C dyes and lakes. The coloring materials are preferably water-soluble. Illustrative nonlimiting examples include the indigoid dye known as FD & C Blue No. 1, and D & C Yellow No. 10. A full recitation of all FD & C colorants and their corresponding chemical structures may be found in the Kirk-Othmer Encyclopedia of Chemical Technology, 3rd Edition, in volume 5 at pages 857–884. A preferred opacifier, titanium dioxide, may be incorporated in amounts up to about 2.0% by weight, preferably less than about 1.0% by weight based on the total weight of the composition and most preferably less than about 0.4% by weight.

Desensitizing agents used to diminish teeth sensitivity such as strontium chloride, potassium nitrate and potassium citrate may also be included in the oral compositions of the present invention at concentrations of from about 0.1 to 10% by weight.

Various other materials may be incorporated in the oral compositions of the invention including whitening agents such as urea peroxide and hydrogen peroxide, preservatives, such as sodium benzoate, chlorophyll compounds and/or ammoniated compounds such as urea, diammonium phosphate, and mixtures thereof. These adjuvants, when present, are incorporated in the compositions in amounts which do not substantially adversely affect the desired properties.

The oral compositions of the present invention may be prepared by suitably mixing the ingredients. By way of example, in the preparation of a mouthrinse, the antimicrobial agent of Formula (III) may be dispersed in a mixture containing for example, alcohol, humectant, surface-active agent, and salts such as sodium fluoride and potassium phosphate, and a flavoring is then added and the resulting combination mixed thoroughly. Dentifrices are prepared in a similar manner with the addition, typically, of a thickener and a polishing agent.

The oral compositions of the present invention may be incorporated into dispersible oral films, oral film forming dentifrices, lozenges, or in chewing gum or other products, e.g. by stirring into a warm gum base or coating the outer surface of a gum base, illustrative of which may be mentioned jelutone, rubber latex, vinylite resins, and the like, desirably with conventional plasticizers or softeners, sugar or other sweeteners or carbohydrates such as glucose, sorbitol and the like.

Oral film forming dentifrices include materials that may be applied to dental and/or oral surfaces in a manner to form a film or coating for reducing physical access to such surfaces by microorganisms, acid, food residues, debris, and the like, and for preventing growth of harmful microorganisms. The resulting oral film thus provides a protective physical barrier and enhances delivery of antimicrobial agents for minimizing attachment, propagation, growth or colonization of bacteria on the dental surfaces. Such compositions may be water-soluble. Suitable oral film forming substances include silicone compounds, aminoalkyl silicones, organopolysiloxanes, dimethyl polysiloxanes, alkyl-dimethicone copolyols, alkoxy-dimethicone copolyols, cyclic siloxane polymers and like substances.

The vehicle or carrier for a tablet or lozenge is desirably a non-cariogenic solid water-soluble polyhydric alcohol (polyol) such as mannitol, xylitol, sorbitol, malitol, a hydrogenated starch hydrolysate, Lycasin, hydrogenated glucose, hydrogenated disaccharides or hydrogenated polysaccharides, in an amount of from about 90 to 98% by weight. Solid salts such as sodium bicarbonate, sodium chloride, potassium bicarbonate or potassium chloride may totally or partially replace the polyol carrier.

Tableting lubricants, in minor amounts of from about 0.1 to 5% by weight, may be incorporated into the tablet or lozenge formulation to facilitate the preparation of both the tablets and lozenges. Suitable lubricants include vegetable oils such as coconut oil, magnesium stearate, aluminum stearate, talc, starch and Carbowax.

Lozenge formulations contain about 2% gum as a barrier agent to provide a shiny surface as opposed to a tablet which has a smooth finish. Suitable non-cariogenic gums include kappa carrageenan, carboxymethyl cellulose, hydroxyethyl cellulose, and the like.

The lozenge or tablet may optionally be coated with a coating material such as waxes, shellac, carboxymethyl cellulose, polyethylene/maleic anhydride copolymer or kappa-carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet and lozenge composition of this invention affords a relatively longer time period of contact of the teeth in the oral cavity with the active ingredients.

Dispersible oral film formulations contain an antimicrobial compound of Formula (III) in a carrier comprising one or more water-soluble polymers in combination with certain ingredients and provides a therapeutic and/or cosmetic effect. The film is coated and dried utilizing existing coating technology and exhibits instant wettability followed by rapid dissolution/disintegration upon administration in the oral cavity.

The foregoing discussion discloses and describes merely exemplary embodiments of the present invention. One skilled in the art will readily recognize from such discussion that various changes, modifications and variations can be made therein without departing from the spirit and scope of the invention as defined in the following claims.

EXAMPLE 1

Mouthrinse Formulation Containing Antimicrobial Compounds of Formula (III)

A mouthrinse composition containing the ingredients and the amounts shown in Table 1 is prepared by mixing the alcohol soluble ingredients 2 and 3 with ethanol. Water is added to the mixture. Water soluble ingredients 4 through 9 are then added and blended thoroughly to the mixture. About 1000 ml of water are added to the mixture to adjust the final volume to yield the mouthrinse composition.

TABLE 1

| Ingredients | % by weight |
| --- | --- |
| 1) Alcohol, USP | 15 |
| 2) Antimicrobial Agents of Formula (III) | 0.05 |
| 3) Flavoring oil | 0.1 |
| 4) Glycerine | 3 |
| 5) Sodium lauryl methyl cocoyl taurate | 0.3 |
| 6) Sodium citrate | 0.08 |
| 7) Citric acid | 0.02 |
| 8) Saccharin sodium | 0.1 |
| 9) FD&C Green #3 | 0.0002 |
| 10) Water, USP | QS to 100 |

EXAMPLE 2

Dentifrice Composition Containing Antimicrobial Compounds of Formula (III)

A dentifrice composition containing the ingredients and the amounts shown in Table 2 is prepared by combining water, a portion of the humectant, the sweetener, the fluoride, and the water soluble buffers together. The remainder of the humectant is separately combined with the gum and then added to the initial mixture. Titanium oxide and silicas are blended and then added to the mixture. The colorant, flavor oil, antimicrobial compounds of Formula (III) and the surfactant are added and blended with the mixture.

TABLE 2

| Ingredients | % by weight |
| --- | --- |
| 1) Glycerine | 6 |
| 2) Sodium carboxymethylcellulose | 1.2 |
| 3) Sorbitol | 40 |
| 4) Sodium monofluoriphosphate, USP | 0.76 |
| 5) Saccharin sodium | 1 |
| 6) Sodium phosphate, dibasic | 0.03 |
| 7) Sodium phosphate, monobasic | 0.25 |
| 8) Silicon dioxide, hydrated | 15 |
| 9) Titanium dioxide | 0.2 |
| 10) Flavor oil | 2 |
| 11) Antimicrobial Agents of Formula (III) | 0.5 |
| 12) FD&C Green #3 | 0.0002 |
| 13) Water, deionized | QS to 100 |

EXAMPLE 3

Deodorant Composition Containing Antimicrobial Compounds of Formula (II)

A deodorant composition containing the ingredients and the amounts shown in Table 3 is prepared by mixing together the polar solvent, volatile nonpolar solvent, and the antimicrobial compounds of Formula (II). Gellants are added to the resulting mixture and agitated. The mixture is heated to a temperature in the range from about 75E to 100E C until the gellants melted and formed a substantially clear and translucent liquid. The resulting liquid mixture is slightly cooled prior to adding the fragrance. The resulting liquid mixture is poured into a suitable container and cooled to yield a solid form composition.

TABLE 3

| Ingredients | % by weight |
| --- | --- |
| 1) Propylene glycol | 30 |
| 2) Glycerine | 2.5 |
| 3) Butyl stearate | 20 |
| 4) Antimicrobial Agents of Formula (II) | 0.5 |
| 5) Propylene glycol monostearate | 15 |
| 6) Water | 32 |

EXAMPLE 4

Antibacterial Soap Composition Containing Antimicrobial Compounds of Formula (II)

An antibacterial soap composition containing the ingredients and the amounts shown in Table 4 is prepared by agitating and mixing the ingredients for thorough blending.

TABLE 4

| Ingredients | % by weight |
| --- | --- |
| 1) Sodium lauryl sulfate | 67 |
| 2) Cocamidopropyl betaine | 15 |
| 3) Glycerine | 1 |
| 4) Propylene glycol | 1 |
| 5) Antimicrobial Agents of Formula (II) | 1 |
| 6) Fragrance | 0.2 |
| 7) Water | QS to 100 |

EXAMPLE 5

Antibacterial Cream or Ointment Composition Containing Antimicrobial Compounds of Formula (II)

An antibacterial cream or ointment composition containing the ingredients and amounts shown in Table 5 is prepared by dissolving the antimicrobial compound of Formula (II) into the solvent and surfactant ingredients. The hydrophobic ingredients are then added to the resulting mixture and blended. The resulting mixture yields an emulsion having a uniform creamy consistency.

TABLE 5

| Ingredients | % by weight |
| --- | --- |
| 1) Glycerine | 6 |
| 2) Propylene glycol | 5.5 |
| 3) Sodium lauryl sulfate | 1 |
| 4) Cetyl alcohol | 4.5 |
| 5) Cetyl palmitate | 4 |
| 6) Steric alcohol | 4.5 |
| 7) Steric acid | 4 |
| 8) White petrolatum | 5 |
| 9) Antimicrobial Agents of Formula (II) | 1 |
| 10) Water, deionized | 64.5 |

What is claimed is:

1. An oral composition comprising an antimicrobial

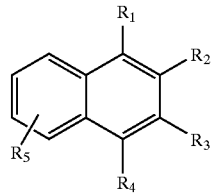

(IIIa)

effective amount of at least one antimicrobial agent having the Formula
wherein
$R_1$ is selected from the group consisting of 2-hydroxycyclohexyl, 3-hydroxycyclohexyl, 4-hydroxycyclohexyl, 2-hydroxycyclopentyl, 3-hydroxcyclopentyl, cyclopentyl, 2-hydroxyphenyl, 3-hydroxyphenyl, and 4-hydroxyphenyl;
$R_2$ is hydroxyl; and
each of $R_3$, $R_4$, and $R_5$ is hydrogen; and
an orally acceptable carrier.

* * * * *